United States Patent
Foidart et al.

(10) Patent No.: US 12,233,074 B2
(45) Date of Patent: Feb. 25, 2025

(54) CONTRACEPTIVE METHODS WITH IMPROVED PEARL INDEX

(71) Applicant: ESTETRA SRL, Liège (BE)

(72) Inventors: Jean-Michel Foidart, Liège (BE); Maud Jost, Liège (BE)

(73) Assignee: ESTETRA SRL, Liège (BE)

( * ) Notice: Subject to any disclaimer, the term of this patent is extended or adjusted under 35 U.S.C. 154(b) by 0 days.

(21) Appl. No.: 18/107,703

(22) Filed: Feb. 9, 2023

(65) Prior Publication Data

US 2023/0248743 A1   Aug. 10, 2023

Related U.S. Application Data

(60) Provisional application No. 63/308,917, filed on Feb. 10, 2022.

(51) Int. Cl.
*A61K 31/585* (2006.01)
*A61K 31/565* (2006.01)
*A61P 15/18* (2006.01)

(52) U.S. Cl.
CPC .......... *A61K 31/585* (2013.01); *A61K 31/565* (2013.01); *A61P 15/18* (2018.01)

(58) Field of Classification Search
CPC .................................... A61K 31/585
USPC ......................................... 514/170
See application file for complete search history.

(56) References Cited

U.S. PATENT DOCUMENTS

| | | |
|---|---|---|
| 7,732,430 B2 | 6/2010 | Bunschoten et al. |
| 8,026,228 B2 | 9/2011 | Coelingh Bennink et al. |
| 11,452,733 B2 | 9/2022 | Taziaux et al. |
| 11,484,539 B2 | 11/2022 | Taziaux et al. |
| 11,666,585 B2 | 6/2023 | Taziaux et al. |
| 2019/0167700 A1 | 6/2019 | Jost et al. |
| 2020/0046729 A1 | 2/2020 | Jost et al. |
| 2022/0211722 A1 | 7/2022 | Foidart |
| 2023/0025785 A1 | 1/2023 | Taziaux et al. |
| 2023/0031329 A1 | 2/2023 | Taziaux et al. |
| 2023/0041304 A1 | 2/2023 | Jost et al. |
| 2023/0073911 A1 | 3/2023 | Taziaux et al. |

FOREIGN PATENT DOCUMENTS

WO   WO-2023/152682 A1   8/2023

OTHER PUBLICATIONS

Andrew M. Kaunitz et al. Bleeding Patterns With Use of an Oral Contraceptive Containing Estetrol and Drospirenone: Pooled Analysis of Phase-3 Clinical Trials Abstract P0640; Int'l J. Obs. Gyn. (FIGO) (Oct. 2021).
Jeffrey T. Jensen et al. "Pooled Phase-3 Analysis of Efficacy and Safety of Estetrol/Drospirenone Combined Oral Contraceptive" Abstract P0638; Int'l J. Obs. Gyn. (FIGO) (Oct. 2021).
K Gemzell-Danielsson et al. "Estetrol-Drospirenone combination oral contraceptive: a clinical study of contraceptive efficacy, bleeding pattern and safety in Europe and Russia," Brit. J. Obs. Gyn. May 20, 2021 DOI: 10.1111/1471-0528.16840: www.bjog.org.
Mitchell D. Creinin et al. "Estetrol-drospirenone combination oral contraceptive: North American phase 3 efficacy and safety results" Contraception 104 (2021) 222-228.
Nexstellis Prescribing Information Approved: Apr. 2021.
Nextstellis Patient Brochure (Nov. 2022).
Nextstellis: Product Monograph; Searchlight Pharma Inc.; Date of Initial Authorization: Mar. 5, 2021.
K Gemzell-Danielsson et al. "Estetrol-Drospirenone combination oral contraceptive: a clinical study of contraceptive efficacy, bleeding pattern and safety in Europe and Russia," Brit. J. Obs. Gyn. Published On-line Aug. 9, 2021 DOI: 10.1111/1471-0528.16840: www.bjog.org.

*Primary Examiner* — Taofiq A Solola
(74) *Attorney, Agent, or Firm* — Foley & Lardner LLP (57) ABSTRACT

Described are methods of providing contraception in a woman having a BMI≥30.0 kg/m², comprising: selecting a woman determined to have a BMI≥30.0 kg/m², and then orally administering to the selected woman a therapeutically effective amount of an estetrol component at a daily dose of from 14 mg to 16 mg, based on the estetrol moiety, and drospirenone at a daily dose of from 2.5 mg to 3.5 mg. Also described are methods of contraception that achieves a Pearl Index of <5 in women having a BMI≥30.0 kg/m², comprising: selecting a woman determined to have a BMI≥30.0 kg/m², and then orally administering to the selected woman a therapeutically effective amount of an estetrol component at a daily dose of from 14 mg to 16 mg, based on the estetrol moiety, and drospirenone at a daily dose of from 2.5 mg to 3.5 mg, wherein the method comprises daily administration of the estetrol component and drospirenone on 24 consecutive days followed by a hormone-free period of 4 consecutive days.

8 Claims, 2 Drawing Sheets

FIG. 1

*This category includes participants with a confirmed pregnancy (pre-treatment, on-treatment, and post-treatment) listed as their primary reason for discontinuation

FIG. 2

CONTRACEPTIVE METHODS WITH IMPROVED PEARL INDEX

CROSS-REFERENCE TO RELATED APPLICATIONS

This application claims priority to U.S. provisional application 63/308,917, filed Feb. 10, 2022, the entire contents of which are incorporated herein by reference.

FIELD

Described are methods of providing contraception with an improved pearl index in women having a body mass index (BMI)≥30.0 kg/m².

BACKGROUND

The following discussion is provided to aid the reader in understanding the disclosure and is not admitted to describe or constitute prior art thereto.

Combined oral contraceptives (COCs) comprising a progestin component and an estrogen component are commonly used for contraception worldwide. The progestin component is primarily responsible for the contraceptive effect, while the main function of the estrogen component is to balance the impact of the progestin on the endometrium. Most COCs contain ethinyl estradiol (EE) as the estrogen component, which is combined with a progestin that may vary from product to product.

COCs comprising estetrol (E4) as the estrogen component and drospirenone (DRSP) as the progestin component have been described in, for example, U.S. Pat. No. 7,732,430. The United States (U.S.) Food and Drug Administration (FDA), the European Medicines Agency, Health Canada, and the Therapeutic Goods Administration in Australia have recently approved the first estetrol (E4)-based COC.

The Pearl Index (PI) is a common calculation used in clinical trials for reporting the effectiveness of a birth control method. In general, a higher PI means a product is less effective at preventing pregnancy compared to a product with a lower PI.

Previously marketed COCs, such as those containing ethinyl estradiol (EE), are less effective in women that are overweight or obese, as indicated by a BMI of 25.0-30.0 kg/m² and ≥30.0 kg/m² respectively. In other words, conventional COCs have a positive association between BMI and PI.

There thus remains a need for methods of providing effective contraception in women having higher BMI levels, including in women having a BMI≥30.0 kg/m².

SUMMARY

The present disclosure provides methods of providing contraception in women having a BMI≥30.0.0 kg/m² and methods of contraception that achieve a Pearl Index with the upper limit of the 95% confidence interval <5 in women having a BMI≥30.0 kg/m².

In one aspect, the present disclosure provides methods of providing contraception in a woman having a BMI≥30.0 kg/m², comprising: selecting a woman determined to have a BMI≥30.0 kg/m², and then orally administering to the selected woman a therapeutically effective amount of an estetrol component at a daily dose of from 14 mg to 16 mg, based on the estetrol moiety, and drospirenone at a daily dose of from 2.5 mg to 3.5 mg.

In some embodiments, the estetrol component is estetrol monohydrate. In some embodiments, the estetrol component is estetrol monohydrate and is administered at a daily dose of 15 mg and the drospirenone is administered at a daily dose of 3 mg.

In some embodiments, the methods may further comprise, prior to the selecting, calculating the BMI of the woman from a measured height and weight of the woman.

In some embodiments, the selecting comprises selecting a woman determined to have a BMI≥30.0 kg/m² and ≤35.0 kg/m².

In some embodiments, the selecting comprises selecting a woman determined to have a BMI≥30.0 kg/m² and determined to be 16-25 years old.

In some embodiments, the methods may comprise daily administration of the estetrol component and drospirenone on 24 consecutive days.

In some embodiments, the methods may further comprise, following the 24 consecutive days of administration of the estetrol component and drospirenone, a hormone-free period of 4 consecutive days.

In some embodiments, the methods may comprise administration according to consecutive 28-day cycles of daily administration of the estetrol component and drospirenone on consecutive days 1-24, followed by a hormone-free period without administration of the estetrol component and drospirenone on consecutive days 25-28.

In another aspect, the present disclosure provides methods of contraception that achieves a Pearl Index of <5 in women having a BMI≥30.0 kg/m², comprising: selecting a woman determined to have a BMI≥30.0 kg/m², and then orally administering to the selected woman a therapeutically effective amount of an estetrol component at a daily dose of from 14 mg to 16 mg, based on the estetrol moiety, and drospirenone at a daily dose of from 2.5 mg to 3.5 mg, wherein the method comprises daily administration of the estetrol component and drospirenone on 24 consecutive days followed by a hormone-free period of 4 consecutive days.

In some embodiments, the methods may further comprise, prior to the selecting, calculating the BMI of the woman from a measured height and weight of the woman.

In some embodiments, the selecting comprises selecting a woman determined to have a BMI≥30.0 kg/m² and ≤35.0 kg/m².

In some embodiments, the method has a Pearl Index of <2.5.

In some embodiments, the selecting comprises selecting a woman determined to have a BMI≥30.0 kg/m² and determined to be 16-25 years old.

In some embodiments, the method has a Pearl Index of <1.

In some embodiments, the methods may comprise 12 cycles of daily administration of the estetrol component and drospirenone on 24 consecutive days, followed by a hormone-free period of 4 consecutive days.

In some embodiments, the methods may comprise 12 consecutive 28-day cycles of daily administration of the estetrol component and drospirenone on consecutive days 1-24 followed by a hormone-free period without administration of the estetrol component and drospirenone on consecutive days 25-28.

In some embodiments, the estetrol component is estetrol monohydrate. In some embodiments, the estetrol component is estetrol monohydrate and is administered at a daily dose of 15 mg and the drospirenone is administered at a daily dose of 3 mg.

The foregoing general description and following detailed description are exemplary and explanatory and are intended to provide further explanation of the disclosure as claimed. Other objects, advantages, and novel features will be readily apparent to those skilled in the art from the following brief description of the drawings and detailed description of the disclosure.

DETAILED DESCRIPTION

The present inventors surprisingly discovered that methods of contraception using E4/DRSP are surprisingly effective in women having higher BMI levels, including women having a BMI≥30.0 kg/m². Thus, described herein in accordance with some embodiments are methods of providing contraception in a woman having a BMI≥30.0 kg/m², comprising: selecting a woman determined to have a BMI≥30.0 kg/m², and then orally administering to the selected woman a therapeutically effective amount of an estetrol component at a daily dose of from 14 mg to 16 mg, based on the estetrol moiety, and drospirenone at a daily dose of from 2.5 mg to 3.5 mg. Also described herein are methods of contraception that achieve a Pearl Index of <5 in women having a BMI≥30.0 kg/m², comprising: selecting a woman determined to have a BMI≥30.0 kg/m², and then orally administering to the selected woman a therapeutically effective amount of an estetrol component at a daily dose of from 14 mg to 16 mg, based on the estetrol moiety, and drospirenone at a daily dose of from 2.5 mg to 3.5 mg, wherein the method comprises daily administration of the estetrol component and drospirenone on 24 consecutive days followed by a hormone-free period of 4 consecutive days.

Thus, as shown herein, E4/DRSP (e.g., 15/3 mg) has a PI well below 5 even at the upper end of the 95% CI, and therefore this COC fulfils the FDA criterion of a very effective COC (Guidance for Industry: Establishing effectiveness and safety for hormonal drug products intended to prevent pregnancy. July, 2019) regardless of BMI.

Definitions

As used herein, "about" when used in conjunction with a measurable value such as a parameter, an amount, a temporal duration, and the like, is meant to encompass variations of up to +/−10% from the specified value. Thus, "about 10" should be understood to include any value from 9 to 11, as well as a value of 10.

As used herein, "effective amount" refers to an amount effective to achieve an intended physiological effect, such as contraception. The physiological effect need not be achieved by a single dose and may be achieved by repeated doses, each considered to be "effective." In the context of contraception "an effective amount" refers to an amount which is effective to suppress ovulation when administered in accordance with an effective regimen. It is emphasized that an "effective amount" will not always achieve the intended physiological effect in every individual subject, even though such dose is deemed to be a therapeutically effective amount by those of skill in the art.

As used herein, "BMI" stands for Body Mass Index, and is defined as body mass of a human subject divided by the square of body height of the human subject, and is expressed in units of kg/m², resulting from mass in kilograms and height in meters.

As used herein, "Pearl Index" or "PI" is a measure of contraceptive efficacy that is calculated as the number of on-treatment pregnancies per 100 woman-years of exposure during at-risk 28-day cycles. Thus, the formula for calculating PI is:

$$PI = \frac{\text{Number of on-treatment pregnancies} \times 13}{\text{Number of women} \times \text{Number of 28-day equivalent cycles of treatment}} \times 100$$

As used herein, an "at risk" cycle refers to a cycle with confirmed intercourse and no other contraceptive method used. As used herein, "exposure" means treatment in accordance with the methods described herein. As used herein, an "on-treatment pregnancy" is reported and confirmed as an on-treatment pregnancy if it is determined that the conception date was ≤7 days after commencement of treatment with E4/DRSP as described herein.

As used herein a woman is a "switcher" when she discontinues the use of one type of hormonal contraceptive to initiate the use of another type of hormonal contraceptive. Optionally, this switch comprises a break in use of hormonal contraceptives of 4 weeks or more. A woman is typically considered as a "switcher" if previous hormonal contraceptive use took place within 3 months prior to E4/DRSP use.

As used herein a woman is a "true new user" when she is in her first year of ever using a hormonal contraceptive.

As used herein a woman is a "starter" when she has discontinued use of hormonal contraceptives for three months or longer.

As noted above, the methods described herein comprise orally administering an estetrol component and drospirenone.

Estetrol

The term "estetrol component" as used herein encompasses estetrol, hydrates thereof, esters thereof, and combinations of any thereof.

The chemical name for estetrol is estra-1,3,5(10)-triene-3,15α,16α,17β-tetrol. Estetrol has a molecular formula of $C_{18}H_{24}O_4$ and a molecular weight of 304.4 g/mol. Estetrol has the following chemical structure:

Examples of suitable estetrol esters include esters wherein the hydrogen atom of at least one of the hydroxyl groups of estetrol has been substituted by an acyl radical of a hydrocarbon carboxylic, sulfonic acid or sulfamic acid of 1-25 carbon atoms.

In some embodiments, the estetrol component is estetrol monohydrate. The chemical name for estetrol monohydrate is estra-1,3,5(10)-triene-3,15α,16α,17α-tetrol monohydrate. It has a molecular formula of $C_{18}H_{24}O_4 \cdot H_2O$ and a molecular weight of 322.4 g/mol, equivalent to 304.4 g/mol (anhydrous). Estetrol monohydrate has the following chemical structure:

Estetrol monohydrate is a white to off-white crystalline solid that is poorly soluble in water and aqueous solutions. It is soluble in methanol, ethanol, sparingly soluble in acetone, and slightly soluble in ethyl acetate and acetonitrile.
Drospirenone Drospirenone has the chemical name (6R,7R,8R,9S,10R, 13S,14S,15S,16S,17S)1,3',4',6,6a,7,8,9,10,11,12,13,14,15, 15a,16-hexadecahydro10,13-dimethylspiro-[17Hdicyclopropa-[6,7:15,16] cyclopenta[a]phenanthrene-17,2'(5H)-furan]-3,5'(2H)-dione). It has a molecular weight of 366.5 g/mol, a molecular formula of $C_{24}H_{30}O_3$, and the following chemical structure:

Drospirenone is a white to almost white or slightly yellow crystalline powder. It is a neutral molecule with slight solubility in water.
Methods of Contraception and Pearl Index As noted above, the present inventors surprisingly discovered that methods of contraception using E4/DRSP are associated with a lower than expected Pearl Index (PI) in women with a BMI of ≥30.0 kg/m². Thus, the present disclosure provides methods of providing contraception in a woman having a BMI≥30.0 kg/m², comprising: selecting a woman determined to have a BMI≥30.0 kg/m², and then orally administering to the selected woman a therapeutically effective amount of an estetrol component at a daily dose of from 14 mg to 16 mg, based on the estetrol moiety, and drospirenone at a daily dose of from 2.5 mg to 3.5 mg. The present disclosure further provides method of contraception that achieves a Pearl Index of <5 in women having a BMI≥30.0 kg/m², comprising: selecting a woman determined to have a BMI≥30.0 kg/m², and then orally administering to the selected woman a therapeutically effective amount of an estetrol component at a daily dose of from 14 mg to 16 mg, based on the estetrol moiety, and drospirenone at a daily dose of from 2.5 mg to 3.5 mg, wherein the method comprises daily administration of the estetrol component and drospirenone on 24 consecutive days followed by a hormone-free period of 4 consecutive days.

Analysis of pooled efficacy data from two parallel, open-label, 13-cycle phase 3 clinical trials discussed in more detail below surprisingly showed strong efficacy in women with a BMI≥30.0 kg/m², as reflected in a Pearl Index of <5. The present disclosure reports for the first time methods of providing contraception that do not have lower contraceptive efficacy in obese women (e.g., having a BMI≥30.0 kg/m² and <35 kg/m²). These results were particularly surprising because previous studies examining other hormonal contraceptives have found an association between obesity and contraceptive failure. In contrast, the data provided herein indicates that the Pearl Index for women aged 16-35 years with a BMI of ≥30.0 kg/m² was less than 2.5 (about 2.27), and that the PI was even lower (about 0.97) for a subpopulation ranging in age from 16-25 years. Prior to the present invention, this high level of efficacy of E4/DRSP in women with a BMI of ≥30.0 kg/m² was not known. A large number of obese patients (15%) were included in the study underlying the present invention, thus establishing the contraceptive efficacy in women with a BMI of ≥30.0 kg/m².

In general, the methods described herein comprise orally administering to a woman with a BMI of ≥30.0 kg/m² a therapeutically effective amount of an estetrol component at a daily dose of from 14 mg to 16 mg, based on the estetrol moiety, and drospirenone at a daily dose of from 2.5 mg to 3.5 mg. In specific embodiments, the estetrol component is estetrol monohydrate. In further specific embodiments, the estetrol component is estetrol monohydrate and is administered at a daily dose of 15 mg and the drospirenone is administered at a daily dose of 3 mg.

As discussed in more detail below, the estetrol component and drospirenone may be administered in separate dosage units, or in a single dosage unit comprising both the estetrol component and drospirenone.

The methods typically will comprise administration according to consecutive 28-day cycles of daily administration of the estetrol component and drospirenone on consecutive Days 1-24 followed by a hormone-free period without administration of the estetrol component and drospirenone on consecutive Days 25-28.

For methods of providing contraception in a woman having a BMI≥30.0 kg/m², the methods comprise selecting a woman determined to have a BMI≥30.0 kg/m², and then orally administering to the selected woman a therapeutically effective amount of an estetrol component at a daily dose of from 14 mg to 16 mg, based on the estetrol moiety, and drospirenone at a daily dose of from 2.5 mg to 3.5 mg. In specific embodiments, the estetrol component is estetrol monohydrate. In further specific embodiments, the estetrol component is estetrol monohydrate and is administered at a daily dose of 15 mg and the drospirenone is administered at a daily dose of 3 mg. As noted above, such methods typically will comprise daily administration of the estetrol component and drospirenone on 24 consecutive days.

In some embodiments, the methods further comprise, prior to the selecting, calculating the BMI of the woman from a measured height and weight of the woman. Calculating the BMI can include measuring the woman's height and weight.

In some embodiments, the selecting comprises selecting a woman determined to have a BMI≥30.0 kg/m² and ≤35 kg/m².

In some embodiments, the selecting comprises selecting a woman determined to have a BMI≥30.0 kg/m² but ≤35 kg/m² and determined to be 16-25 years old.

For methods of contraception that achieve a Pearl Index of <5 in women having a BMI≥30.0 kg/m², the methods comprise selecting a woman determined to have a BMI≥30.0 kg/m², and then orally administering to the selected woman a therapeutically effective amount of an estetrol component at a daily dose of from 14 mg to 16 mg, based on the estetrol moiety, and drospirenone at a daily dose of from 2.5 mg to 3.5 mg, with daily administration of the estetrol component and drospirenone on 24 consecutive days followed by a hormone-free period of 4 consecutive days. Thus, such methods typically will comprise administration according to consecutive 28-day cycles of daily administration of the estetrol component and drospirenone on consecutive Days 1-24 followed by a hormone-free period without administration of the estetrol component and drospirenone on consecutive Days 25-28.

In accordance with such methods, the BMI of the woman may be calculated prior to the selection of the woman for treatment with E4/DRSP. Calculating the BMI can include measuring the woman's height and weight.

In some embodiments, the selecting comprises selecting a woman determined to have a BMI≥30.0 kg/m² and ≤35 kg/m².

In some embodiments, the selecting comprises selecting a woman determined to have a BMI≥30.0 kg/m² and determined to be 16-25 years old.

The FDA criterion for establishing "effective contraception" requires a PI below 5, and here, the data indicates that even the upper limit of a 95% CI for E4/DRSP is still well below 5, thus underscoring the efficacy of this combination across various populations. For the purposes of any of the foregoing methods or embodiments of contraception in women having a BMI≥30.0 kg/m², the method can achieve a Pearl Index of <5.00, <4.95, <4.90, <4.85, <4.80, <4.75, <4.70, <4.65, <4.60, <4.55, <4.50, <4.45, <4.40, <4.35, <4.30, <4.25, <4.20, <4.15, <4.10, <4.05, <4.00, <3.95, <3.90, <3.85, <3.80, <3.75, <3.70, <3.65, <3.60, <3.55, <3.50, <3.45, <3.40, <3.35, <3.30, <3.25, <3.20, <3.15, <3.10, <3.05, <3.00, <2.95, <2.90, <2.85, <2.80, <2.75, <2.70, <2.65, <2.60, <2.55, <2.50, <2.45, <2.40, <2.35, <2.30, <2.25, <2.20, <2.15, <2.10, <2.05, or <2.00. In some embodiments, the disclosed methods may achieve a Pearl Index of <2.5. In some embodiments, the methods may achieve a Pearl Index of about 5 or less. In some embodiments, the methods may achieve a Pearl Index of about 4.5 or less. In some embodiments, the methods may achieve a Pearl Index of about 4 or less. In some embodiments, the methods may achieve a Pearl Index of about 3.5 or less. In some embodiments, the methods may achieve a Pearl Index of about 3 or less. In some embodiments, the methods may achieve a Pearl Index of about 2.5 or less. In some embodiments, the methods may achieve a Pearl Index of about 2.27.

As used herein, a method that achieves a Pearl Index of a stated value refers to a method that achieves a Pearl Index of the stated value with a 95% confidence interval, assuming an underlying Poisson distribution.

In some embodiments, the PI for women having a BMI≥30.0 kg/m² treated in accordance with the methods described herein is not clinically different from the PI for women having a BMI<30.0 kg/m² treated in accordance with the methods described herein.

According to some embodiments, no significant differences of the PI for women having a BMI≥30.0 kg/m² compared to women having a BMI<30.0 kg/m² are observed when performing a multivariate analysis or a univariate analysis like the Chi-square test.

In some embodiments, further selection based on age may be performed to further improve the Pearl Index. For example, treatment of women with a BMI of ≥30.0 kg/m² that are 16-25 years in age may achieve a Pearl Index of less than 1 (e.g., a Peal Index of about 0.97). Treatment of women with a BMI of ≥30.0 kg/m² that are 26-35 years in age may achieve a Pearl Index of less than 3.5, less than 3.25, or about 3.10.

Additionally or alternatively, in accordance with any of the foregoing embodiments, the methods may achieve a lower Pearl Index in women with a BMI of ≥30.0 kg/m² as compared to methods using ethinyl estradiol (EE)-based contraceptives, such as EE 10 µg/norethindrone acetate 1 mg, EE 13 µg/segesterone acetate 150 mg, and EE 30 µg/levonorgestrel 120 µg (daily transdermal system). Additionally or alternatively, in accordance with any of the foregoing embodiments, the methods may achieve a lower Pearl Index in women with a BMI of ≥30.0 kg/m² as compared to treatment with a progestin-only contraceptive, such as DRSP 4 mg.

While the methods described herein contemplate daily administration of the estetrol component and drospirenone on consecutive Days 1-24 followed by a hormone-free period without administration of the estetrol component and drospirenone on consecutive Days 25-28, it should be understood that minor interruptions in the administration schedule may occur without significantly impacting the overall contraceptive effectiveness of the methods, and such aberrations are encompassed by the present disclosure. Unintended interruptions may occur. In general, if one administration is missed, the missed dosage form(s) should be taken as soon as possible and the next administration should still occur at the regularly scheduled time, even if this results in two administrations in a single day.

In order to achieve maximum contraceptive effectiveness, it may be advisable to administer the dosage form(s) comprising the estetrol component and drospirenone at around the same time each day. Further, the first administration (i.e., Day 1 of the first treatment cycle) is typically administered on the first day of menstruation or, in the case of a switcher, on the first day when a new cycle of treatment for the woman's prior oral contraceptive would have started or, in others words, at the time when the first pill of a pill pack of the previous oral contraceptive pill would have been due.

In some embodiments, the hormone-free period (without administration of the estetrol component and drospirenone) on, for example, consecutive Days 25-28, may comprise taking a dosage form (e.g., pill, tablet, etc.) that does not contain an estetrol component and drospirenone (e.g., an inert or inactive pill, tablet, etc.).

The woman being administered the contraceptive may be a true new user (i.e., she has not previously used an oral contraceptive), a switcher, or a starter.

Oral Pharmaceutical Compositions

Oral pharmaceutical compositions useful for carrying out the methods described herein are not particularly limited; suitable non-limiting examples are described herein.

As noted above, the estetrol component and drospirenone may be formulated in separate compositions or in a single composition comprising both the estetrol component and drospirenone. Typically, the estetrol component and drospirenone are formulated in oral dosage units that provide a daily dose of one or both of the estetrol component and drospirenone, such as from 14 mg to 16 mg of the estetrol component, based on the estetrol moiety, and 2.5 to 3.5 mg of drospirenone. In specific embodiments, the estetrol component and drospirenone are formulated together in oral dosage units that provide a daily dose of both the estetrol component and drospirenone, such as from 14 mg to 16 mg of the estetrol component, based on the estetrol moiety, and 2.5 to 3.5 mg of drospirenone. In further specific embodiments, the estetrol component is estetrol monohydrate and the estetrol monohydrate and drospirenone are formulated together in oral dosage units that contain 15 mg of estetrol monohydrate and 3 mg of drospirenone.

The oral dosage units may be in the form of tablets, capsules, cachets, pellets, pills, powders, or granules capsules comprising dry compositions, or capsules that contain a liquid composition, such as an oil, in which the estetrol component is dissolved or dispersed. Tablets, pellets, and pills can, optionally, be film-coated to achieve a desired release profile.

Dry composition(s) may further comprise one or more pharmaceutically acceptable excipients such as, but not limited to, one or more binders (e.g. hydroxypropylmethyl cellulose, polyvinyl pyrrolidone, other cellulosic materials and starch), diluents (e.g. lactose and other sugars, starch, dicalcium phosphate and cellulosic materials), disintegrating agents (e.g. starch polymers and cellulosic materials) and lubricating agents (e.g., stearates and talc), etc. For example, pharmaceutical excipients or inactive ingredients that may be used to prepare a COC dosage form as described herein can include, but are not limited to, corn starch, lactose monohydrate, magnesium stearate, povidone, and sodium starch glycolate. Dry composition(s) may be prepared by wet granulation, using an aqueous solution or an organic solution, or by direct compression.

Dry or liquid composition(s) may further comprise one more pharmaceutically acceptable excipients such as, but not limited to, one or more of antioxidants, stabilizers, preservatives, coloring agents, flavouring agents, etc.

As noted above, the estetrol component may be one or more substances selected from estetrol, hydrates of estetrol, and esters of estetrol. In specific embodiments, the estetrol component is estetrol monohydrate.

In some embodiments, the amount of the estetrol component may be 14.0, 14.1, 14.2, 14.3, 14.4, 14.5, 14.6, 14.7, 14.8, 14.9, 15.0, 15.1, 15.2, 15.3, 15.4, 15.5, 15.6, 15.7, 15.8, 15.9, or 16 mg, based on the estetrol moiety. In some embodiments, the amount of the estetrol component is 14.2 mg based on the estetrol moiety. When the estetrol component is estetrol monohydrate, 15 mg estetrol monohydrate may provide 14.2 mg based on the estetrol moiety.

In some embodiments, the amount of drospirenone may be 2.5, 2.6, 2.7, 2.8, 2.9, 3.0, 3.1, 3.2, 3.3, 3.4, or 3.5 mg. In some embodiments, the amount of drospirenone is 3.0 mg. For the purposes of the disclosed methods and compositions, the dosage forms necessary to complete a 28-day treatment cycle may be provided in a single blister pack containing (i) 24 active tablet comprising an estetrol component and drospirenone, and (ii) 4 inert tablets that do not contain an estetrol component or drospirenone.

The methods and compositions have been described above with reference to a number of exemplary embodiments. Modifications and alternative implementations of some parts or elements are possible, and are included in the scope of the disclosure. The following examples are provided to illustrate certain embodiments of the disclosed methods and compositions. It should be understood, however, that the invention is not to be limited to the specific conditions or details described in these examples.

Example 1—Pearl Index and Efficacy Analysis

Overview: Pooled efficacy data from two phase 3 clinical trials using estetrol (E4) monohydrate 15 mg and drospirenone (DRSP) 3 mg (E4/DRSP) demonstrated excellent contraceptive efficacy in daily users across the entire cohort of participants. In particular, efficacy outcomes from two phase 3 contraceptive trials with E4/DRSP were pooled, and the Pearl Index (PI) in at-risk cycles (cycles with confirmed intercourse and no other contraceptive method used) among participants aged 16-35 years was assessed. PI was calculated based on age, contraceptive history, and body mass index (BMI). Multivariable analysis using Cox regression was used to assess the impact of potential confounding factors. The analyses included 3,027 participants, of whom 451 (14.9%) had a BMI≥30.0 kg/m$^2$. The pooled PI was 1.52 (95% confidence interval [CI] 1.04-2.16), and the unadjusted pooled PI in participants 16-25 years and 26-35 years was 1.61[0.94-2.57]) and 1.43 [0.78-2.40]), respectively. In new starters and switchers the PI was 1.88[1.09-3.00]) and 1.24[0.68-2.08]), respectively. Surprisingly, when PI was stratified by BMI, the results showed efficacy across BMI values, with BMI≥30.0 kg/m$^2$, 25.0-29.9 kg/m$^2$ and <25.0 kg/m$^2$ achieving PIs of 2.27[0.83-4.94], 2.19[1.05-4.03], and 1.14[0.64-1.88]), respectively (p=0.1683).

As further detailed below, E4/DRSP was found to be surprisingly effective in women having a high BMI, such as a BMI≥30.0 kg/m$^2$. The present invention therefore provides for the first time an ability to advise women having a BMI≥30.0 kg/m$^2$ that the E4/DRSP treatment regimen described herein should be highly effective for them, which may improve compliance and promote continuation of treatment.

Materials and Methods

This pooled analyses was performed on data from two multi-center, open-label, non-comparator phase 3 clinical trials that evaluated the contraceptive efficacy and safety of E4 15 mg/DRSP 3 mg oral contraceptive pills in healthy reproductive age women.

The studies enrolled healthy, heterosexually active, pre-menopausal participants (aged 16-50 years in the U.S./Canada trial [n=1,864]; aged 18-50 years in the Europe/Russia trial [n=1,553]) according to previously described inclusion and exclusion criteria (Creinin et al., Contraception, 2021, 104(3):222-228 and Danielsson et al., *BJOG*, 2022, 129(1):63-71), which included a BMI of 18.0-35.0 kg/m$^2$. Participants could have switched from a previous hormonal contraceptive method except for injectable contraceptives. Eligible participants received E4 15 mg (as monohydrate, equivalent to 14.2 mg anhydrous)/DRSP 3 mg once daily in a 24/4-day regimen for up to thirteen 28-day cycles. Switchers from another COC started study treatment when the next pill pack of the previous formulation would have been due, and new users started treatment on the first day of menstruation.

Investigators conducted follow-up visits at Cycles 2, 4, 7, 10, and at end of treatment (Cycle 13 or discontinuation). Participants completed a daily paper diary to record medication intake, use of other contraceptives, and sexual intercourse. During each study visit, a study coordinator reviewed the diary and collected empty study drug packets to check treatment compliance. Any day without a diary entry was considered to be a day with no pill intake. Participants completed a urine pregnancy test before first pill intake, following any treatment cycle without withdrawal bleeding, and at the end of treatment.

All participants who used at least one dose of E4/DRSP and had at least one follow-up contact were included in the analysis. The primary efficacy endpoint was Pearl Index (PI) in participants aged 16-35 years (at screening), calculated as the number of pregnancies per 100 woman-years of exposure during at-risk 28-day cycles. Any reported/confirmed pregnancy was considered an "on-treatment pregnancy" if the investigator estimated the conception date to be ≤7 days after the last intake of study drug (with E4/DRSP or placebo pill), based on the FDA definition. Cycles were considered at-risk if the participant self-reported in her diary use of the study drug, having intercourse ≥1 time in that cycle, and no use of other contraceptive methods (including condoms and emergency contraception). In addition, the overall PI was evaluated using the EMA definition (conception date ≤2 days after the last intake of study drug), method-failure PI (pregnancy occurred with self-reported correct E4/DRSP intake and no use of excluded medications known to interact with oral contraceptives), life-table pregnancy rates, and PIs according to subcategories.

PIs were calculated by age group (16-25 years, 26-35 years, 36-50 years), along with further subcategorization by contraceptive history (starters, switchers), BMI class (<25.0 kg/m$^2$, ≥25.0 to 29.9 kg/m$^2$, ≥30.0 kg/m$^2$), race (Asian, Black, Other, White) and smoking status (former smokers, current smokers, non-smokers) for age groups 16-25 years and 26-35 years. Starters included persons who had not used hormonal contraception within three months prior to E4/DRSP initiation (including those who had never used hormonal contraception), while all others were defined as switchers.

For the primary efficacy group aged 16-35 years, PIs were further evaluated by subgroups of age (16-25 years vs. 26-35 years), BMI (≥30.0 kg/m$^2$ vs. <30.0 kg/m$^2$), contraceptive history (starter vs. switcher), gravidity (at least one pregnancy before study vs. no pregnancies), smoking status (current or former smoker vs. never smoker), race (Asian or Black or Other vs. White), region (U.S./Canada vs. Europe/Russia) and compliance (low compliance vs. high compliance). Treatment compliance was defined as the reported number of pills taken divided by the expected number of pills taken based on the duration of participation, with ≥99% of expected pills defined as high compliance. Compliance was also evaluated by subgroups.

PIs were calculated with a 95% confidence interval (CI) assuming an underlying Poisson distribution. Life-table analysis (Kaplan-Meier estimates and 95% CIs) was used to calculate the cumulative pregnancy rate of on-treatment and method-failure pregnancies through 13 cycles. To adjust for the effects of confounding on these multiple efficacy comparisons in the primary efficacy group, we performed multivariable analysis using a Cox regression model with hazard ratios (HR) and 95% Wald Confidence Limits to assess confounding by age, BMI, past hormonal contraceptive use, gravidity, smoking status, race, region, and compliance. Non-parametric tests (Wilcoxon for 2 levels and Kruskal Wallis for more than 2 levels) were used for subgroup comparisons for self-reported compliance. All statistical analyses were performed using SAS® software (version 9.4) for Windows®.

Results

Figure 1:
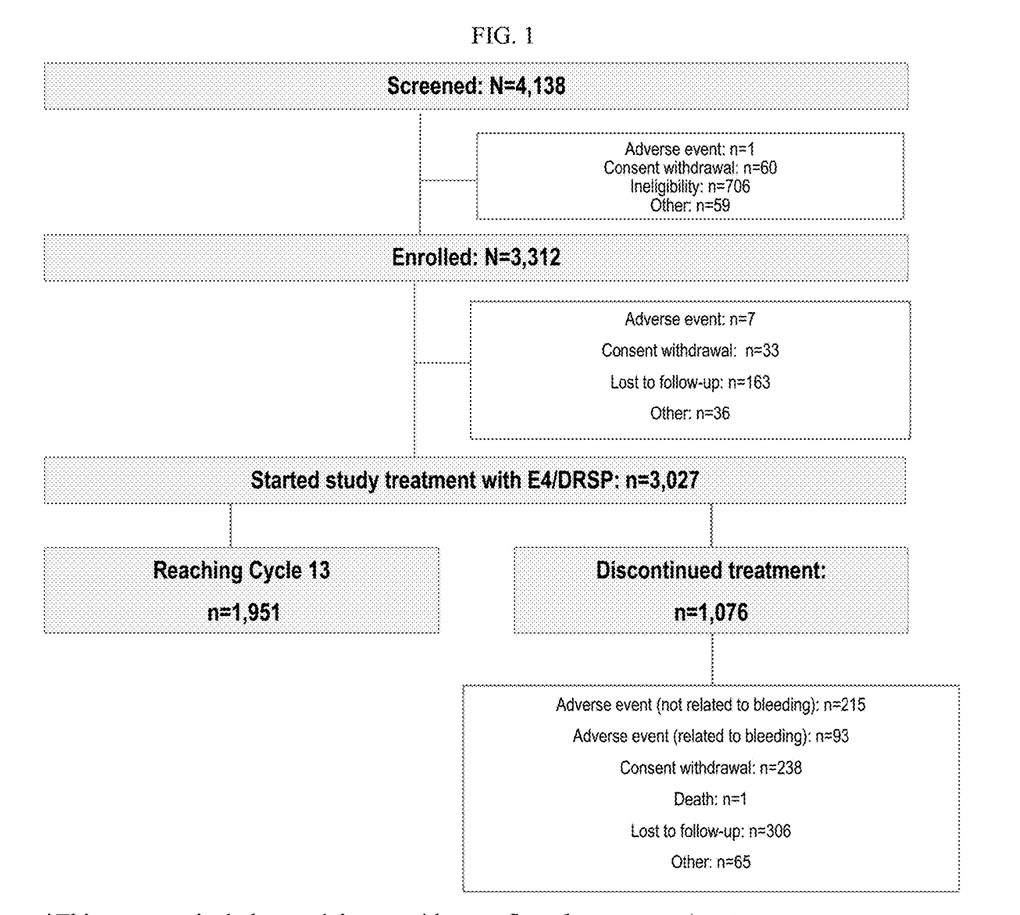
FIG. 1 shows disposition of participants 16-35 years.
Figure 2:
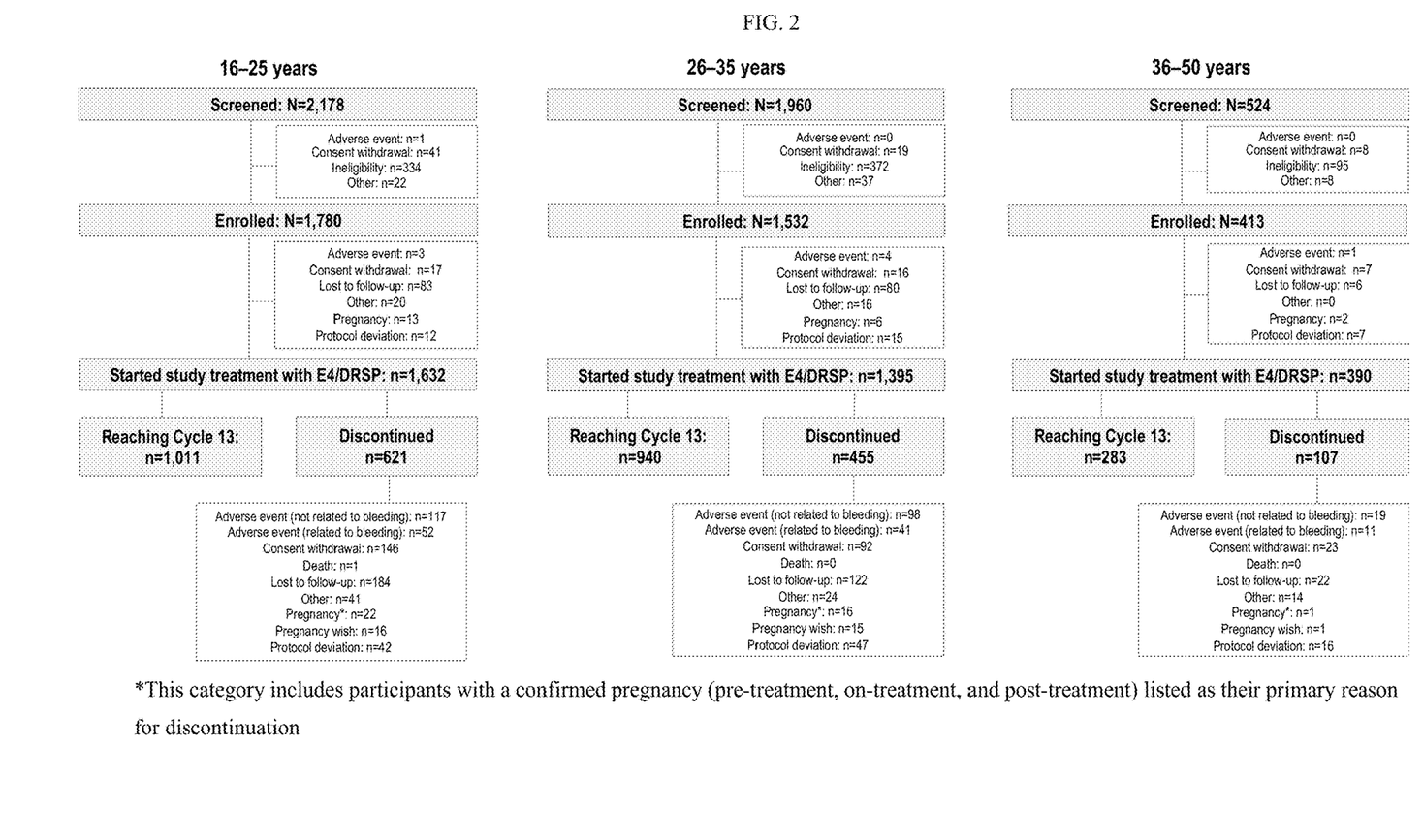
FIG. 2 shows disposition of participants based on age categorizations (16-25 years, 26-35 years, 36-50 years).

The primary efficacy population included 1,674 participants aged 16-35 years in the U.S./Canada trial and 1,353 participants aged 18-35 years in the Europe/Russia trial. Participant characteristics are presented in Table 1. Overall, 1,951 (64.5%) participants completed cycle 13. The most common reasons for discontinuation were lost to follow-up (n=306 [10.1%]), consent withdrawal (n=238 [7.9%]), and adverse events not related to bleeding (n=215 [7.1%]) (FIG. 1).

TABLE 1

| Demographics pooled population (16-35 years) | | | |
|---|---|---|---|
| | 16-25 years (n = 1,632) | 26-35 years (n = 1,395) | Total 16-35 years (n = 3,027) |
| Age (years) | 21.8 ± 2.2 | 29.7 ± 2.8 | 25.4 (4.6) |
| Body mass index | 23.8 ± 4.2 | 25.2 ± 4.6 | 24.5 ± 4.4 |
| <25.0 kg/m$^2$ | 1,113 (68.2) | 765 (54.8) | 1,878 (62.0) |
| 25.0 to 29.9 kg/m$^2$ | 333 (20.4) | 365 (26.2) | 698 (23.1) |
| ≥30.0 kg/m$^2$ | 186 (11.4) | 265 (19.0) | 451 (14.9) |
| Gravidity | | | |
| Nulligravid | 1,378 (84.4) | 606 (43.4) | 1,984 (65.6) |
| History of dysmenorrhea | 480 (29.4) | 388 (27.8) | 868 (28.7) |
| Past hormonal contraceptive use | | | |
| >3 months before screening (starter) | 779 (47.7) | 714 (51.2) | 1,493 (49.3) |
| None (starter) | 376 (23.0) | 245 (17.6) | 621 (20.5) |
| ≤3 months before screening (switchers) | 853 (52.3) | 681 (48.8) | 1,534 (50.7) |
| Race | | | |
| Asian | 53 (3.2) | 37 (2.7) | 90 (3.0) |
| Black | 145 (8.9) | 189 (13.5) | 334 (11.0) |
| Other* | 45 (2.8) | 50 (3.6) | 95 (3.1) |
| White | 1,389 (85.1) | 1,119 (80.2) | 2,508 (82.9) |
| Region | | | |
| Canada | 83 (5.1) | 60 (4.3) | 143 (4.7) |
| Europe | 680 (41.7) | 433 (31.0) | 1,113 (36.8) |
| Russia | 113 (6.9) | 127 (9.1) | 240 (7.9) |
| United States | 756 (46.3) | 775 (55.6) | 1,531 (50.6) |
| Smoking status | | | |
| Current smoker | 242 (14.8) | 226 (16.2) | 468 (15.5) |
| Former smoker | 90 (5.5) | 153 (11.0) | 243 (8.0) |
| Never smoker | 1,300 (79.7) | 1,016 (72.8) | 2,316 (76.5) |

Data presented as mean ± standard deviation or n (%)
*Includes American Indian or Alaskan Native, Native Hawaiian or other Pacific Islanders and Other Among 16-35-year olds, the median self-reported compliance with daily pill intake was 100% (interquartile range [IQR] 99.5-100%) across all cycles. No differences in median compliance were observed between BMI subgroups, smokers vs non-smokers and age categories 16-25 years vs 26-35 years, all with median compliance of 100% with the lower IQR>99%. Higher compliance rates were found across all cycles in switchers (median 100% [IQR 99.5-100%]) vs starters (median 100% [IQR 99.2-100%]) (p=0.0008), in White (median 100% [IQR 99.5-100%]) vs Black (median 100% [IQR 98.1-100%]) (p<0.0001) and in Europe (median 100% [IQR 99.7-100%]) vs US participants (median 100% [IQR 99.2-100%]) (p=0.0003). Other race and region (Russia and Canada) categories were too small to allow for meaningful comparisons.

The pooled PI in the primary efficacy group was 1.52 (95% CI 1.04-2.16) pregnancies per 100 women-years based on 31 pregnancies in 2,837 women with 26,455 cycles of use. The method-failure PI was 0.84 (0.49-1.34) pregnancies per 100 women-years. Cumulative 13-cycle life-table pregnancy rates were 1.28% (0.83%-1.73%) overall and 0.73% (0.38%-1.08%) for method-failure pregnancies (Table 2).

The PI was 1.61 (0.94-2.57) pregnancies per 100 women-years in participants 16-25 years and 1.43 (0.78-2.40) pregnancies per 100 women-years in those 26-35 years (Table 2).

TABLE 2

Pearl Index and Cumulative Pregnancy Rate

|  | 16-25 years | 26-35 years | Total 16-35 years |
|---|---|---|---|
| PI for 'at risk cycles' according to FDA[1] | | | |
| Subjects (n) | 1,518 | 1,319 | 2,837 |
| Cycles (n) | 13,759 | 12,696 | 26,455 |
| On-treatment pregnancies (n) | 17 | 14 | 31 |
| PI (95% CI) | 1.61 (0.94-2.57) | 1.43 (0.78-2.40) | 1.52 (1.04-2.16) |
| PI for 'at risk cycles' according to EMA[2] | | | |
| Subjects (n) | 1,573 | 1,362 | 2,935 |
| Cycles (n) | 15,013 | 13,725 | 28,738 |
| On-treatment pregnancies (n) | 17 | 14 | 31 |
| PI (95% CI) | 1.47 (0.86-2.36) | 1.33 (0.72-2.22) | 1.40 (0.95-1.99) |
| Method failure PI for 'at risk cycles' according to FDA[1,3] | | | |
| Subjects (n) | 1,518 | 1,319 | 2,837 |
| Cycles (n) | 13,759 | 12,696 | 26,455 |
| On-treatment pregnancies (n) | 9 | 8 | 17 |
| PI (95% CI) | 0.85 (0.39-1.61) | 0.82 (0.35-1.61) | 0.84 (0.49-1.34) |
| Cumulative pregnancy rate at cycle 13[4] | | | |
| Cumulative on-treatment pregnancy rate (% [95% CI]) | 1.29 (0.80-2.08) | 1.26 (0.75-2.13) | 1.28 (0.83-1.73) |
| Cumulative on-treatment method failure pregnancy rate (% [95% CI]) | 0.69 (0.36-1.34) | 0.77 (0.38-1.54) | 0.73 (0.38-1.08) |

CI: confidence interval;
EMA: European Medicines Agency;
FDA: Food and Drug Administration;
PI: Pearl Index
[1]At risk cycle FDA: no other methods of birth control (including condoms and emergency contraception), and intercourse confirmed, pregnancy considered 'on-treatment' when estimated date of conception was ≤7 days after last study treatment
[2]At risk cycles EMA: regardless of intercourse, no other methods of birth control (including condoms and emergency contraception), pregnancy considered 'on-treatment' when estimated conception date was ≤2 days after last study treatment
[3]Method failure: excluding pregnancies due to user failure, i.e., not taking E4/DRSP as per protocol during the conception cycle, or co-medication use interacting with combined oral contraceptives
[4]Calculated using Kaplan-Meier life-table analysis Notably, in women aged 16-35 years, the PIs across BMI classes were similar, with results for BMI<25.0 kg/m$^2$, 25.0–29.9 kg/m$^2$ and ≥30.0 kg/m$^2$ being 1.14 [0.64-1.88], 2.19 [1.05–4.03] and 2.27 [0.83-4.94], respectively (p=0.1683). See Table 3, below. Although the highest PI value was observed in women aged 26-35 years with a BMI≥30.0 kg/m$^2$ (3.10 [1.01-7.24]), that PI still reflects a high level of efficacy (i.e., a PI lower than 5). The lowest PI was observed in women aged 26-35 years with a BMI in the normal range (<25.0 kg/m$^2$) (0.71 [0.19-1.83]).

Starters had a PI of 1.88 [1.09-3.00], and switchers had a PI of 1.24 [0.68-2.08]. The highest PI was noted for starters aged 16-25 years (2.63 [1.36-4.60]) and the lowest PI was seen in switchers 16-25 years (0.83 [0.27-1.94]).

TABLE 3

Unadjusted Pearl Index by Subgroups in Pooled Analysis

| Variable | Statistic | 16-25 years | 26-35 years | Total 16-35 years |
|---|---|---|---|---|
| Body mass index | | | | |
| <25.0 kg/m$^2$ | Subjects, n | 1,044 | 727 | 1,771 |
| | Cycles | 9,809 | 7,275 | 17,084 |
| | On-treatment pregnancies | 11 | 4 | 15 |
| | Pearl Index (95% CI) | 1.46 (0.73-2.61) | 0.71 (0.19-1.83) | 1.14 (0.64-1.88) |
| 25.0 to 29.9 kg/m$^2$ | Subjects, n | 311 | 345 | 656 |
| | Cycles | 2,610 | 3,325 | 5,935 |
| | On-treatment pregnancies | 5 | 5 | 10 |
| | Pearl Index (95% CI) | 2.49 (0.81-5.81) | 1.95 (0.63-4.56) | 2.19 (1.05-4.03) |
| ≥30.0 kg/m$^2$ | Subjects, n | 163 | 247 | 410 |
| | Cycles | 1,340 | 2,096 | 3,436 |
| | On-treatment pregnancies | 1 | 5 | 6 |
| | Pearl Index (95% CI) | 0.97 (0.025-5.40) | 3.10 (1.01-7.24) | 2.27 (0.83-4.94) |
| Past hormonal contraceptive use | | | | |
| Starter* | Subjects, n | 704 | 664 | 1,368 |
| | Cycles | 5,924 | 5,859 | 11,783 |
| | On-treatment pregnancies | 12 | 5 | 17 |
| | Pearl Index (95% CI) | 2.63 (1.36-4.60) | 1.11 (0.36-2.59) | 1.88 (1.09-3.00) |
| Switcher† | Subjects, n | 814 | 655 | 1,469 |
| | Cycles | 7,835 | 6,837 | 14,672 |
| | On-treatment pregnancies | 5 | 9 | 14 |
| | Pearl Index (95% CI) | 0.83 (0.27-1.94) | 1.71 (0.78-3.25) | 1.24 (0.68-2.08) |
| Race | | | | |
| Asian | Subjects, n | 48 | 34 | 82 |
| | Cycles | 352 | 332 | 684 |
| | On-treatment pregnancies | 1 | 1 | 2 |
| | Pearl Index (95% CI) | 3.69 (0.09-20.58) | 3.92 (0.10-21.82) | 3.80 (0.46-13.73) |
| Black | Subjects, n | 119 | 165 | 284 |
| | Cycles | 795 | 1,161 | 1,956 |
| | On-treatment pregnancies | 9 | 3 | 12 |
| | Pearl Index (95% CI) | 14.72 (6.73-27.94) | 3.36 (0.69-9.82) | 7.98 (4.12-13.93) |
| Other§ | Subjects, n | 41 | 44 | 85 |
| | Cycles | 312 | 380 | 692 |
| | On-treatment pregnancies | 0 | 1 | 1 |
| | Pearl Index (95% CI) | 0 (.-15.37) | 3.42 (0.09-19.06) | 1.88 (0.05-10.47) |
| White | Subjects, n | 1,310 | 1,076 | 2,386 |
| | Cycles | 12,300 | 10,823 | 23,123 |
| | On-treatment pregnancies | 7 | 9 | 16 |
| | Pearl Index (95% CI) | 0.74 (0.30-1.52) | 1.08 (0.49-2.05) | 0.90 (0.51-1.46) |
| Smoking status | | | | |
| Current smoker | Subjects, n | 221 | 215 | 436 |
| | Cycles | 1,991 | 2,057 | 4,048 |
| | On-treatment pregnancies | 3 | 4 | 7 |
| | Pearl Index (95% CI) | 1.96 (0.40-5.72) | 2.53 (0.69-6.47) | 2.25 (0.90-4.63) |
| Former smoker | Subjects, n | 83 | 140 | 223 |
| | Cycles | 660 | 1,229 | 1,889 |
| | On-treatment pregnancies | 2 | 2 | 4 |
| | Pearl Index (95% CI) | 3.94 (0.48-14.23) | 2.12 (0.26-7.64) | 2.75 (0.75-7.05) |
| Never smoker | Subjects, n | 1214 | 964 | 2,178 |
| | Cycles | 11,108 | 9,410 | 20,518 |
| | On-treatment pregnancies | 12 | 8 | 20 |
| | Pearl Index (95% CI) | 1.40 (0.73-2.45) | 1.10 (0.48-2.18) | 1.27 (0.77-1.96) |

CI: confidence interval
*Past contraceptive use, >3 months before screening (starters) and none (true new users)
†Past contraceptive use within 3 months before screening (switchers)
§Includes American Indian or Alaskan Native, Native Hawaiian or other Pacific Islanders and Other In multivariable analysis of markers of efficacy in the primary efficacy group (data not shown), we found clinically important and statistically significant associations of pregnancy risk in women with a history of prior pregnancy (HR: 3.61 [1.56-8.38]), Black race (HR: 4.61 [1.97-10.80]), age 16-25 years (HR: 2.37 [1.09-5.15]), and low compliance (HR: 4.21 [2.04-8.66]). No significant association of pregnancy risk was observed in women with a BMI≥30.0 kg/m$^2$ compared to women with a BMI<30.0 kg/m$^2$.

Overall, no clinically important differences were found in the unadjusted PIs for the primary efficacy group age categories with further stratification by subgroups (BMI, past hormonal contraceptive use, race, and smoking status) (see Table 3). The lack of clinically important differences across different BMI groups was particularly surprising, especially in view of reports that the efficacy of other COCs decreases with increasing BMI.

Discussion

The pooled PI data for E4/DRSP in 16-35 year olds of 1.52 (with a CI of 1.04-2.16) and life-table contraceptive protection of 98.7% demonstrated high contraceptive efficacy over 1 year of use. While direct comparison to other contraceptive formulations require caution, other recently FDA-approved combined hormonal contraceptives have reported PIs of 2.92 [1.94-4.21] (ethinyl estradiol (EE) 10 µg/norethindrone acetate 1 mg), 2.98 [2.13-4.06] (EE 13 µg/segesterone acetate 150 mg), and 3.5 [1.8-5.2]) and 5.7 [3.0-8.4] (EE 30 µg/levonorgestrel 120 µg daily transdermal system). Additionally, a recently approved DRSP 4 mg progestin-only pill has a reported PI of 4.0 [2.3-6.4]. Indeed, more recently approved oral, transdermal and vaginal contraceptives tend to have higher PIs than those approved decades ago.

The results reported here provide evidence of high contraceptive efficacy across a diverse group of users, including in women with a BMI≥30.0 kg/m². The strengths of this pooled analyses include a large number of participants and a diverse population, including women with BMI≥30.0 kg/m². Although small PI differences were identified within subgroups, all remain in a highly acceptable (e.g., highly effective) range.

As noted above, it was surprising that this study did not find an association between obesity and lower efficacy of E4/DRSP in the multivariable analysis. The inclusion of a relatively large number (15%) of obese participants in the analysis supports the validity of the conclusion that the methods provide high contraceptive efficacy in this patient subgroup. (The majority of obese participants were enrolled in the U.S. study). This is in contrast to previous studies examining efficacy of other hormonal contraceptives that have found an association between obesity and contraception failure. These findings are important for appropriately selecting patients and providing effective contraception for women with a BMI of ≥30.0 kg/m².

What is claimed is:

1. A method of contraception that achieves a Pearl Index of <2.5 in women 16-25 years old having a BMI≥30.0 kg/m², comprising:
    selecting a woman 16-25 years old and determined to have a BMI≥30.0 kg/m², and then
    orally administering to the selected woman a therapeutically effective amount of an estetrol component comprising an estetrol moiety at a daily dose of from 14 mg to 16 mg, based on the estetrol moiety, and drospirenone at a daily dose of from 2.5 mg to 3.5 mg,
    wherein the method comprises daily administration of the estetrol component and drospirenone on 24 consecutive days followed by a hormone-free period of 4 consecutive days.

2. The method of claim 1, further comprising, prior to the selecting, calculating the BMI of the woman from a measured height and weight of the woman.

3. The method of claim 1, wherein the selecting comprises selecting a woman determined to have a BMI≥30.0 kg/m² and ≤35.0 kg/m².

4. The method of claim 1, wherein the method has a Pearl Index of <1.

5. The method of claim 4, wherein the method comprises 12 cycles of daily administration of the estetrol component and drospirenone on 24 consecutive days, followed by a hormone-free period of 4 consecutive days.

6. The method of claim 4, wherein the method comprises 12 consecutive 28-day cycles of daily administration of the estetrol component and drospirenone on consecutive days 1-24 followed by a hormone-free period without administration of the estetrol component and drospirenone on consecutive days 25-28.

7. The method of claim 1, wherein the estetrol component is estetrol monohydrate.

8. The method of claim 1, wherein the estetrol component is estetrol monohydrate and is administered at a daily dose of 15 mg, based on the estetrol moiety, and the drospirenone is administered at a daily dose of 3 mg.

* * * * *